Figure 2A:
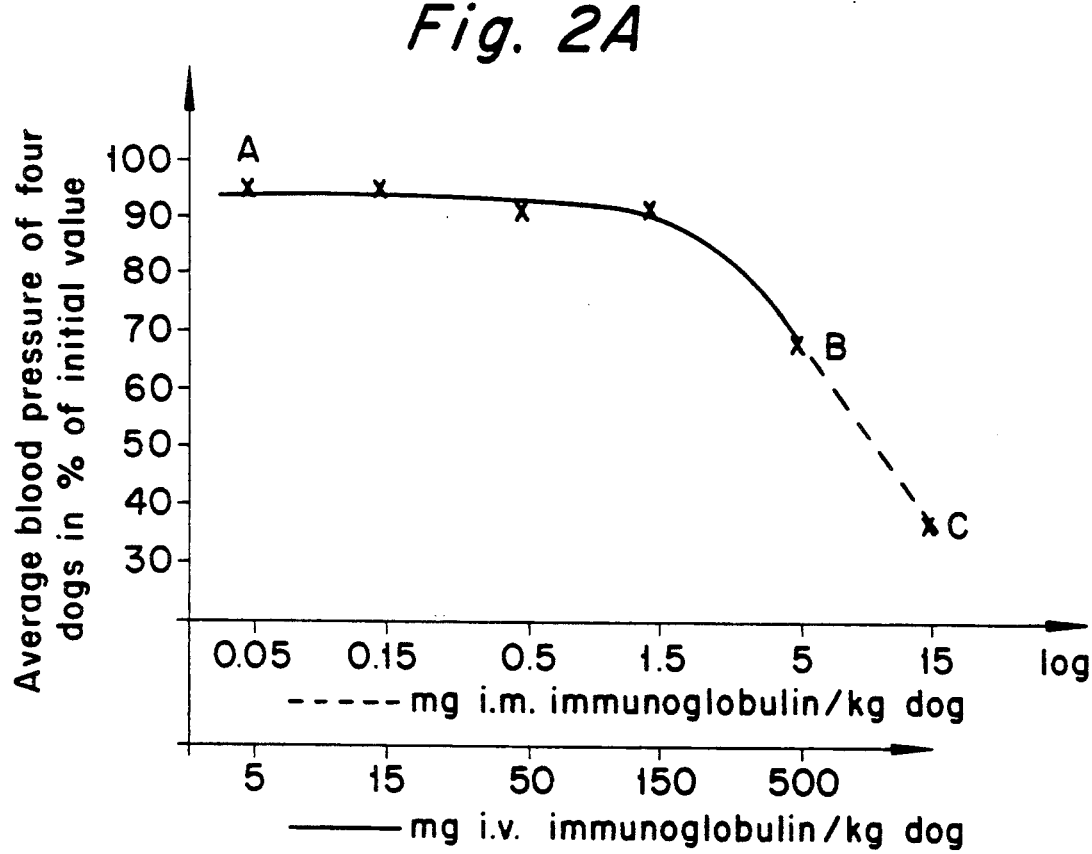
Figure 2B:
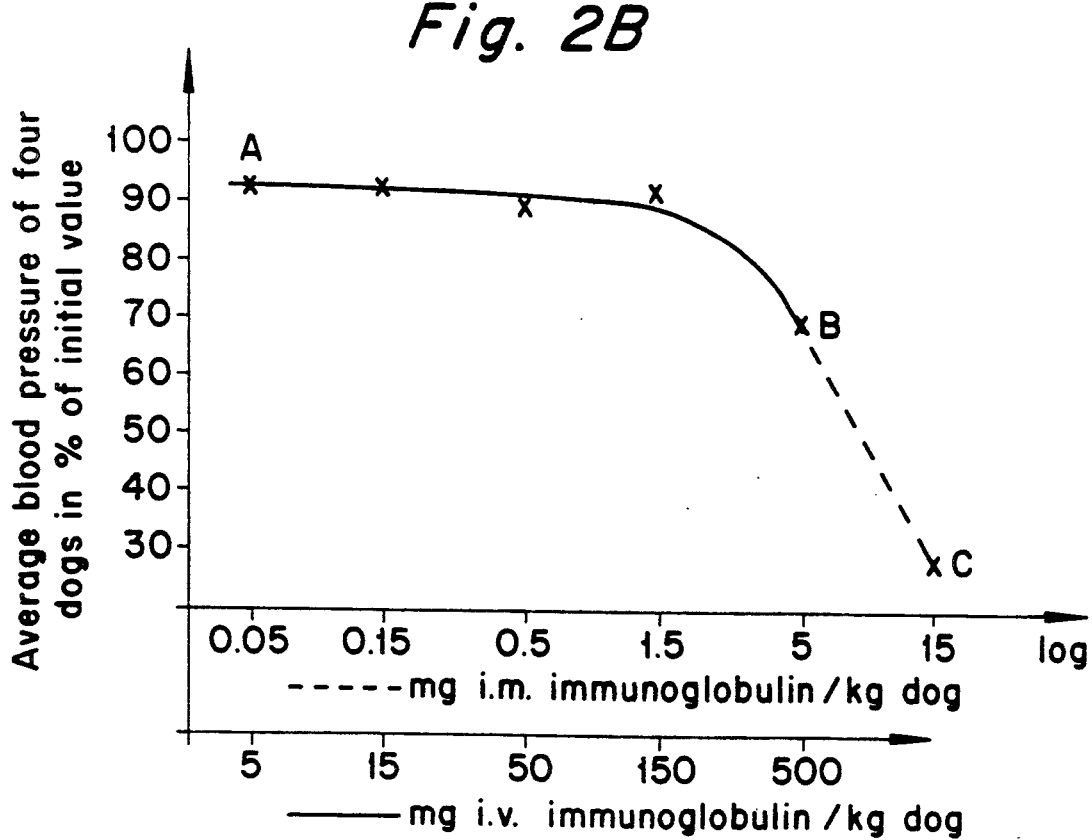
Figure 3:
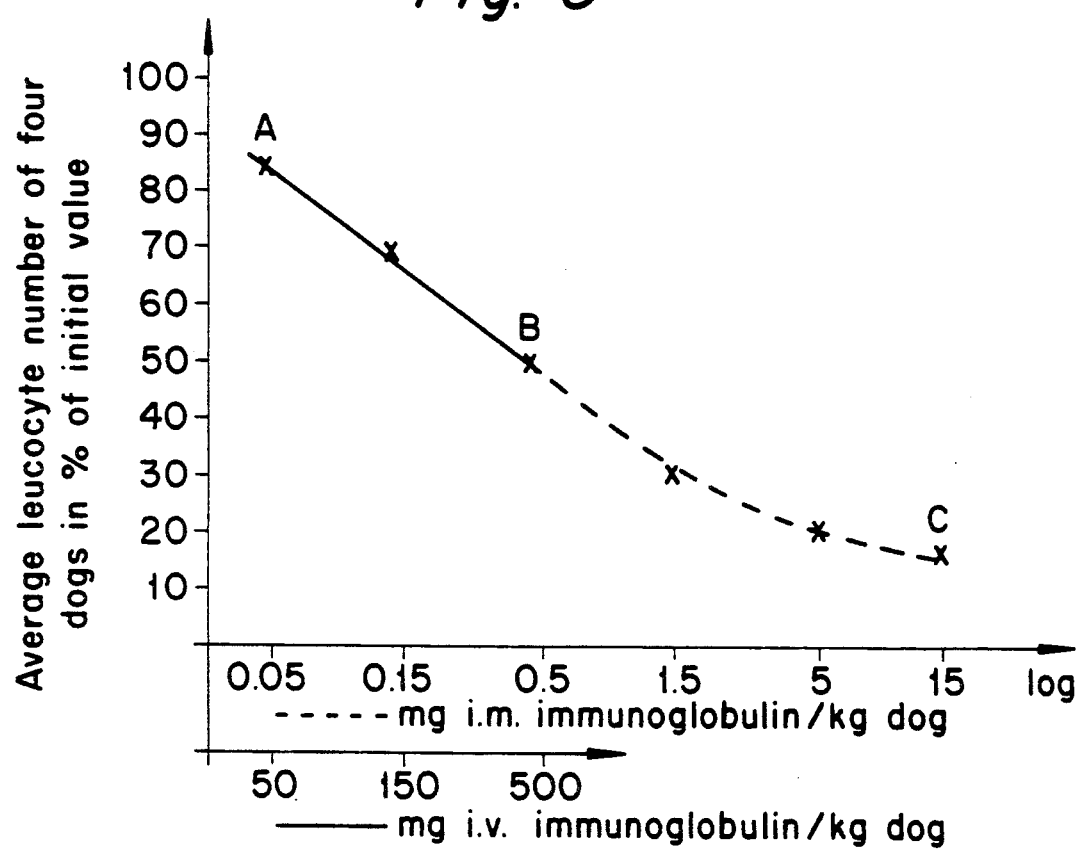
Figure 4:
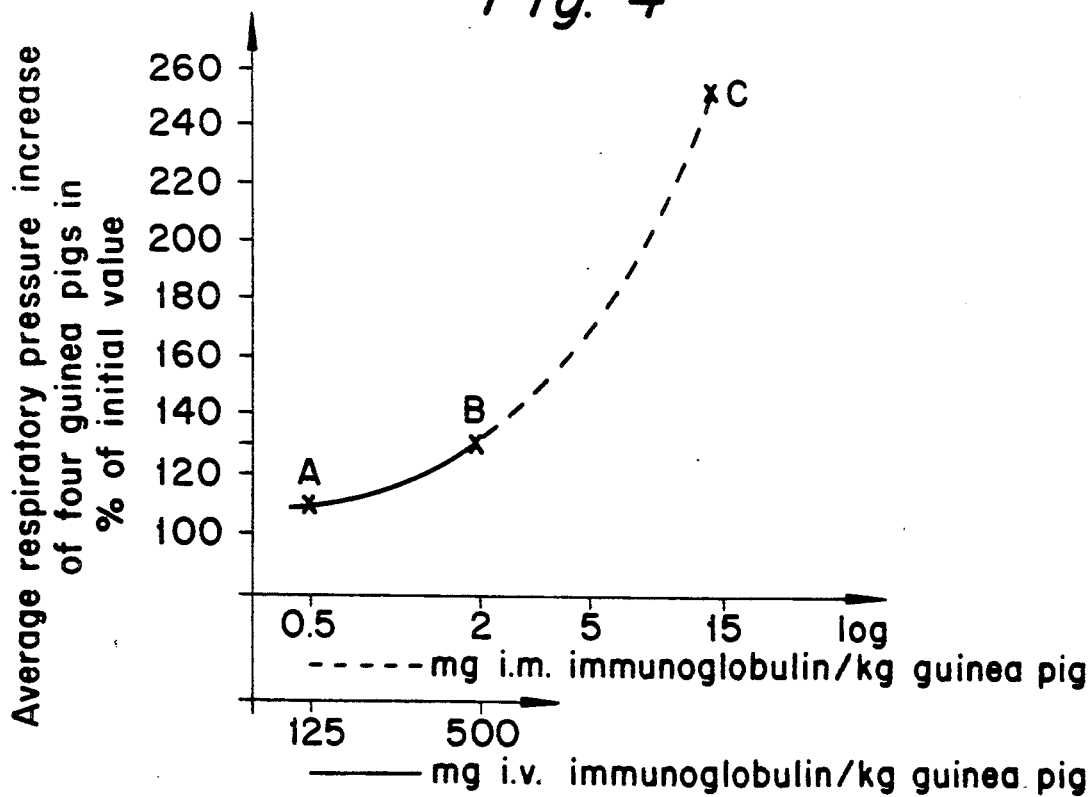

United States Patent [19]

Eibl et al.

[11] Patent Number: 5,122,373
[45] Date of Patent: Jun. 16, 1992

[54] IMMUNOGLOBULIN-G-CONTAINING FRACTION

[75] Inventors: Johann Eibl; Yendra Linnau; Otto Schwarz, all of Vienna, Austria

[73] Assignee: Immuno Aktiengesellschaft, Vienna, Austria

[21] Appl. No.: 569,535

[22] Filed: Aug. 20, 1990

Related U.S. Application Data

[63] Continuation of Ser. No. 216,150, Jul. 7, 1988, abandoned, which is a continuation-in-part of Ser. No. 930,063, Nov. 12, 1986, abandoned, which is a continuation of Ser. No. 584,932, Feb. 29, 1984, abandoned.

[30] Foreign Application Priority Data

Mar. 16, 1983 [AT] Austria ............................. A929/83
Mar. 16, 1983 [AT] Austria ............................. A930/83

[51] Int. Cl.$^5$ ............................................. A61K 39/395
[52] U.S. Cl. .................................. 424/85.8; 530/390.5
[58] Field of Search ................... 424/85.8; 530/387

[56] References Cited

U.S. PATENT DOCUMENTS

| 4,276,283 | 6/1981 | Eibl et al. | 424/85.8 |
|---|---|---|---|
| 4,296,027 | 10/1981 | Condie | 260/112 |
| 4,384,993 | 5/1983 | Sato et al. | 424/85.8 |
| 4,476,109 | 10/1984 | Kimura et al. | 424/85.8 |
| 4,482,483 | 11/1984 | Curry et al. | 424/85.8 |
| 4,499,073 | 2/1985 | Tenold | 424/85.8 |

FOREIGN PATENT DOCUMENTS

| 383737 | 1/1987 | Austria . |
|---|---|---|
| 132284 | 9/1984 | Denmark . |
| 0112909 | 10/1984 | European Pat. Off. . |
| 601135 | 1/1985 | Japan . |

OTHER PUBLICATIONS

Intravenous Immunoglobulin: Prevention and Treatment of Disease; NIH Consensus Development Conference; May 21,23, 1990.

Immune Globulin (Human), Intravenous; IVEEGAM; Issues May 1988; Immuno (Canada) Ltd., Windsor, Ontario.

Primary Examiner—Howard E. Schain
Assistant Examiner—Choon Park Koh
Attorney, Agent, or Firm—Burns, Doane, Swecker & Mathis

[57] ABSTRACT

An immunoglobulin-G-containing fraction from human or animal plasma comprising monomeric IgG molecules as well as at least 70% gammaglobulins, destined for intravenous application.

The fraction has a low anticomplementary activity and is substantially free of vasoactive and leucopenically active as well as bronchospastic substances.

6 Claims, 3 Drawing Sheets

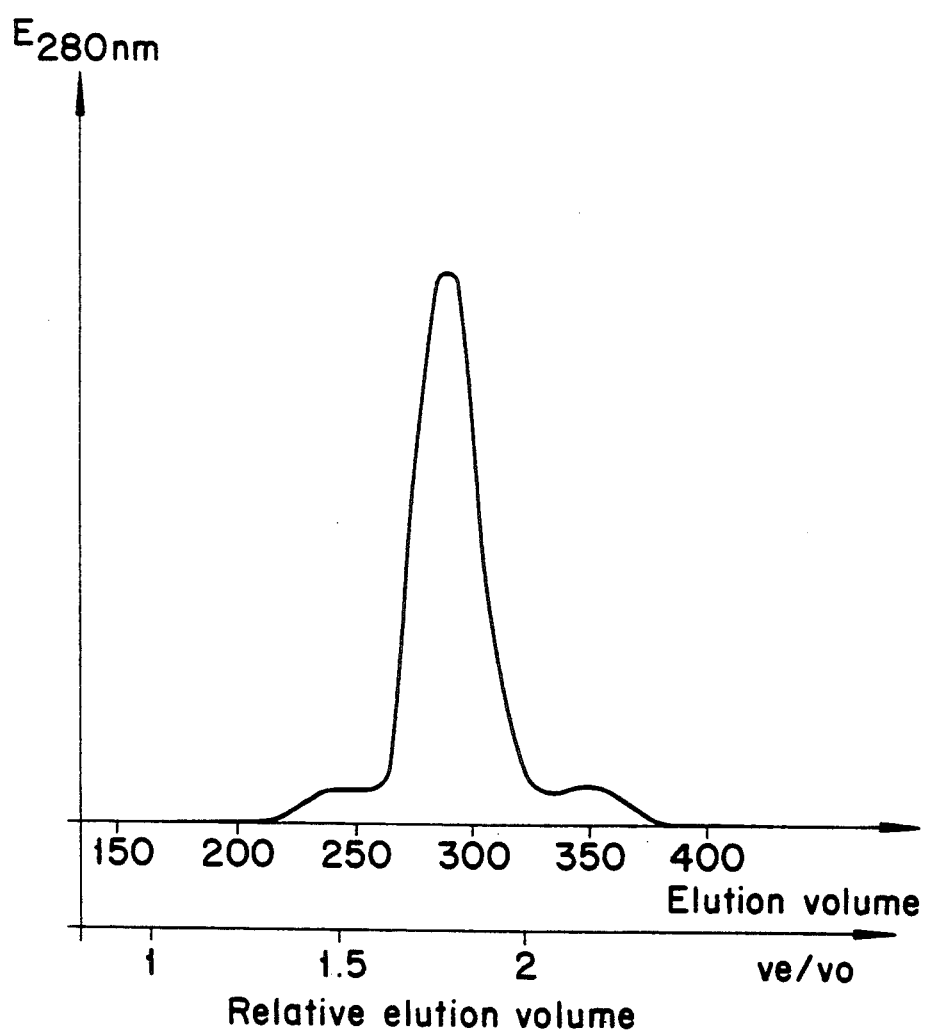

IMMUNOGLOBULIN-G-CONTAINING FRACTION

This application is a continuation of application Ser. No. 07/216,150, filed Jul. 7, 1988, now abandoned which is a continuation-in-part of U.S. Ser. No. 930,063, filed Nov. 12, 1986, now abandoned which is a continuation of Ser. No. 584,932, filed Feb. 29, 1984, now abandoned.

The invention relates to an immunoglobulin-G-containing fraction from human or animal plasma, comprising monomeric IgG molecules and suited for intravenous application.

Immunoglobulin-containing preparations may be applied in case of primary and secondary immune defects, A-gammaglobulinemia or hypogammaglobulinemia, antibody deficiency syndrome, virus infections or bacterial infections.

For obtaining immunoglobulin-containing preparations from human or animal plasma, various methods are already known, e.g. the precipitation with ethanol (J. L. Oncley, M. Melin, D. A. Richart, J. W. Cameron and P. M. Gross, J. Am. Chem. Soc. 71, 541 (1949) as well as modified ethanol methods according to H. F. Deutsch, L. J. Gosting, R. A. Alberty and J. W. Williams, J. Biol. Chem. 164, 109 (1946) as well as P. Kistler and H. Nitschmann, Vox Sanguinis 7, 414 (1962).

Furthermore, a method is known according to which immunoglobulin is precipitated from plasma by means of ammonium sulfate and polyethyleneglycol (A. Polson, G. M. Potgieter, J. F. Largrier, G. E. F. Mears and F. J. Jourbet, Biochim. Biophys. Acta. 82, 463 (1964). According to other methods, the use of ion exchangers has been suggested (E. A. Peterson and H. A. Sober, J. Am. Chem. Soc. 78, 751 (1956)).

These methods had the disadvantage that the obtained preparations were suited for intramuscular application only. With intravenous application, they exhibited undesired side reactions, such as vasoactive effects.

Therefore, efforts have been made to reduce side reactions or side effects, to which end immunoglobulin-containing preparations were treated with soluble proteolytic enzymes, such as pepsin, plasmin, papain and others (German patent No. 1,148,037). However, by this treatment the molecule structure of the immunoglobulins is changed, resulting in a shortened biologic half-life period. It was also found out that enzyme residues remain in the preparations, thereby contaminating the same. The storability is accordingly low, the danger of a progressing proteolytic cleavage is great.

In U.S. Pat. No. 4,276,283 a method for the production of an intravenously administrable immunoglobulin preparation is described, in which a combined purification with ammonium sulfate and polyethyleneglycol is carried out in the presence of a soluble carbohydrate or of a polyol. It is true that vasoactive side effects have been eliminated, yet an improvement in terms of safety and reproducibility in case of intravenous application is still desirable.

Among the prior art, also the Japanese patent applications published under Nos. 56-7721 and 56-15215 as well as German Offenlegungsschrift No. 32 20 309 are to be mentioned, which have as their objects methods for the production of intravenously applicable immunoglobulin preparations. The treatment is to be effected with immobilized plasmin or immobilized pepsin, yet the results attainable thereby are not satisfactory, either, because the preparations have an undesiredly high anticomplementary activity.

The invention aims at avoiding the disadvantages and difficulties described and has as its object to provide an immunoblobulin-containing fraction from human or animal plasma, which is intravenously applicable and free of side effects in an optimum manner. This freedom is to cover also undesired leucopenic and bronchospastic side effects. Furthermore, the immunoglobulin-G-containing fraction according to the invention is to exhibit a very low anticomplementary activity.

This object is achieved according to the invention in that the monomeric-IgG-molecules-comprising fraction contains at least 90% IgG molecules capable of binding to protein A of staphylococcus aureus, has a low anticomplementary activity and is substantially free of vasoactive and leucopenically active as well as bronchospastic substances, expressed by the following characteristic features:

a) the vasoactive effect in dog test as an average of four animals comprising a blood pressure decrease by 30% at the most, is detectable only at a dose of more than 500 mg/kg body weight, b) the leucopenic effect in dog test as an average of four animals comprising a decrease in the number of leucocytes of 50% at the most, is detectable only at a dose of more than 500 mg/kg body weight, and c) the bronchospastic effect in guinea pig test as an average of four animals comprising an increase in the respiratory pressure of 30% at the most, is detectable only at a dose of more than 500 mg/kg body weight.

The determination of the monomeric IgG molecules is effected by gel permeation chromatography (gel filtration) according to H. Determann, "Gel-Chromatographie", Springer Verlag, Berlin, 1967, in the following manner:

The molecules are separated according to their molecular weight. Molecules that are larger than the largest pores in the swollen gel cannot penetrate into the gel and are eluted first (the corresponding elution volume being $V_o$). Smaller molecules penetrate into the gel pores and hence migrate more slowly (the corresponding elution volume being $V_e$). Thus, the elution volume ($V_e$) is a characteristic parameter of a substance. The relative elution volume $V_e/V_o$ of a substance is independent of the geometric column dimensions and the column. The determination is carried out, e.g., by filling a separation column of 2.6 cm diameter and 100 cm length with a gel, e.g., agarose polyacrylamide (tradename Ultrogel AcA 34), that has been swollen in a sodiumphosphate-sodiumchloride buffer (PBS), pH 7.0, 50 mg of an immunoglobulin preparation are applied onto the column and eluted with sodiumphosphate-sodium-chloride buffer, pH 7.0, at a flow rate of 20 ml/h.

The eluates are collected in 4.5 ml fractions and the elution curve is detected at 280 nm by means of a UV detector. On account of the elution diagram, the individual components are pooled and the elution volume as well as the protein concentration are determined.

The immunoglobulins that have a relative elution volume $V_e/V_o$ of between 1.30 and 2.20 are denoted as monomeric IgG molecules and, according to the invention, usually amount to at least 90% of the total protein. In this connection, it is noted that the IgG molecules that have a $V_e/V_o$ of 1.30 to 1.65 are denoted as dimer IgGs; however, since they are in a reversible equilibrium with the monomeric IgG molecule having a $V_e/V_o$ of 1.66 to 2.20, they are to be considered as monomers (cf. J. S. Finlayson, B. L. Armstrong and A. M. Young, Acta Radiologica Supplementum 310, (1971), 114).

The determination of the functionally intact IgG molecules, i.e. the IgG molecules capable of binding to protein A of staphylococcus aureus, is carried out according to an affinity chromatography method with protein A Sepharose (FEBS Letters, Vol. 28, 1972, 73 et seq.; H. Hjelm, K. Hjelm, J. Sjöquist, "Protein A from Staphylococcus aureus, its Solution by Affinity Chromatography and its Use as an Immunosorbent for Isolation of Immunoglobulins"). This method is based on the fact that protein A from staphylococcus aureus gets into interaction with the IgG molecules from subgroups IgG 1, 2 and 4, binding the same. The functionally active positions are the $C_H2$ and $C_H3$ regions, which are parts of the H-chain of the IgG molecules.

The pooled fractions $V_e/V_o$ of 1.30 to 2.20 from the molecular weight determination by means of gel filtration (Diagram I) are adjusted to a certain protein concentration, 10 mg protein of this preparation being chromatographed over 10 ml protein A Sepharose, immobilized protein A. The bound IgGs 1, 2 and 4 are eluted with a sodium citrate-citric acid buffer, pH 3.0. Then the bound and the unbound IgGs are calculated.

According to one embodiment, the fraction according to the invention has such a low anticomplementary activity that it requires no less than 40 mg protein to neutralize one C'H-50-unit, determined and calculated by a modified method substantially based on the method described in "Public Health Monograph" No. 74; Standardized Diagnostic Complement Fixation Method and Adaptation to Microtest, Washington, 1965, and E. A. Kabat and M. Mayer, Experimental Immunochemistry; 2nd Ed. Thomas Springfield 1961.

By electrophoretic determination, at least 95% of gammaglobulin is detected in some of the fractions according to the invention. The determination is effected according to Michael D. Gebott, Beckman Microzone Electrophoresis Manual, Beckman Instruments, Inc. 1977, 015-083630-C.

Characteristic of the immunoglobulin-G-containing fractions produced according to the invention, in addition, are their pharmacological properties: for, they are substantially free of vasoactive and leucopenically active as well as bronchospastic substances, expressed by the following characteristic features:
a) the vasoactive effect in dog test as an average of four animals, i.e. a blood pressure decrease by 30% at the most, is detectable only at a dose of more than 500 mg/kg body weight,
b) the leucopenic effect in dog test as an average of four animals, i.e. a decrease in the number of leucocytes of 50% at the most, is detectable only at a dose of more than 500 mg/kg body weight, and
c) the bronchospastic effect in guinea pig test as an average of four animals, i.e. an increase in the respiratory pressure of 30% at the most, is detectable only at a dose of more than 500 mg/kg body weight.

The vasoactive effect is determined in the following manner:

In test animals (hybrids of both sexes) the vena jugularis and the arteria carotis are dissected upon narcotization. Before anaesthesia, a fasting time of at least 12 hours is fixed. Per test substance four qualified dogs are required, i.e. such dogs which, upon intraarterial application of standardized intramuscularly applicable immunoglobulin ("standard substance") exhibit a vasoactive effect (blood pressure decrease) of at least 30% at a dosage of 50 mg/kg body weight. This standardized intramuscularly applicable immunoglobulin is prepared according to the initially mentioned method by J. L. Oncley, M. Melin, D. A. Richart, J. W. Cameron and P. M. Gross, J. Am. Chem. Soc. 71, 541 (1949). Dogs which do not show any reaction to the standard substance cannot be used for comparative tests.

From the standard substance, 160 mg are dissolved in 1 ml aqua ad injectabilia and diluted to 16.7 mg/ml with isotonic NaCl solution. The dissolved material is used within four hours.

The intravenously applicable immunoglobulin G according to the invention is dissolved with aqua ad injectabilia such that 1 ml contains 165 mg protein. The dissolved material is used within four hours.

The animals are anaesthesized with an intravenous single dose of 40 mg/kg Nembutal (barbiturate), and the vena jugularis externa, after division, is dissected on the lower rim of the mandible, a catheter being bound in. Thereupon, the arteria carotis is laid bare from the same skin incision and a catheter is bound in. After dissection of the arteria it is waited for 30 min in order to gain stable initial values. By means of a pressure transducer, the central venous pressure is measured via the deep venous catheter and the arterial blood pressure is measured via the shallow arterial catheter. Via the arterial catheter, at first the immunoglobulin G i.v. applicable according to the invention and then the standard substance are injected.

During the whole time the experiment is being carried out the systolic and the diastolic blood pressures are recorded via the arterial catheter by means of a pressure transducer.

The blood pressure mean value (systolic and diastolic) as well as the mean value of the number of leucocytes prior to injection of the test substance and the standard substance are determined. The maximum blood pressure decrease is determined by measuring the blood pressure over 20 min after injection of the test substances.

The vasoactive effect of the immunoglobulin G i.v. applicable according to the invention is established by injecting 500 mg/kg body weight of dog and comparing the average systolic and diastolic blood pressure decreases in percent in four dogs with the blood pressure decreasing effect of the i.m. applicable standard substance.

The determination of the leucopenic activity is carried out in the following manner:

In test animals (hybrid dogs of both sexes) the vena jugularis and the arteria carotis are dissected upon narcotization. Before anaesthesia, a fasting time of at least 12 hours is fixed. Per test substance four qualified dogs are required, which, upon intraarterial application of standardized intramuscularly applicable immunoglobulin (standard substance) exhibit a leucopenic effect (leucocyte decrease) of at least 50% at a dosage of 50 mg/kg body weight. Dogs which do not show any reaction to the standard substance cannot be used for comparative tests.

The preparation of the test animals and test substances is effected in the same way as described above.

To investigate the leucocyte number, blood samples are drawn. For the first blood sample, 40 μl blood are admixed with 20 ml Isotone II ® (COULTER) and six droplets Zapoglobin ® (COULTER) and measured in the Coulter counter. Subsequently, further blood samples are drawn after 10, 15, 16, 17, 18 and 19 min to determine the number of leucocytes. Then 500 mg immunoglobulin/kg body weight of i.v. applicable immunoglobulin G are immediately injected intraarterially within 90 s. Further blood samples are drawn 1, 2, 3, 4, 5, 7, 10, 15 and 20 min after injection. After 20 min 50 mg immunoglobulin/kg body weight of the standard substance are injected within 90 s. Blood samples are again drawn after 1, 2, 3, 4, 5, 7, 10, 15 and 20 min.

The maximum decrease in the leucocyte number is determined by assessment of the blood samples drawn 1, 2, 3, 4, 5, 7, 10, 15 and 20 min after injection of the sample.

The leucopenic effect of i.v. applicable immunoglobulin G is determined by injecting 500 mg/kg body weight of dog and comparing the average leucocyte decrease in percent in four dogs with the leucopenic effect of the i.m. applicable standard substance.

The determination of the bronchospastic (respiratory pressure increasing) effect in guinea pigs is effected in the following manner:

In test animals (male guinea pigs) the trachea is dissected in the region of the larynx upon narcotization. After intubation the test animal is respirated by means of a respirator at a respiratory volume corresponding to the body weight of the animal and at a respiration frequency of 80/min. Thereafter, the arteria carotis is dessected bare from the same skin incision. Upon intraarterial injection of the test substance, the respiratory pressure is continuously measured.

For the test, laboratory-bred guinea pigs of the male sex having a body weight of between 500 and 700 g are used. Per test substance four qualified guinea pigs are required, which, upon intraarterial application of standardized i.m. applicable immunoglobulin (standard substance) exhibit an increase in the respiratory pressure by at least 30% at a dosage of 50 mg/kg body weight. Guinea pigs which do not show any reaction to the standard substance cannot be used for comparative tests.

From the standard substance, 160 mg are dissolved in 1 ml aqua ad injectabilia and diluted to 16.7 mg/ml with isotonic NaCl solution. The dissolved material is used within four hours.

The immunoglobulin G i.v. applicable according to the invention is dissolved with aqua ad injectabilia such that 1 ml contains 165 mg protein. The dissolved material is used within four hours.

The animals are narcotized; then the trachea is dissected in the region of the larynx, a tracheal cannula being bound in. By means of a respirator, the test animal is respirated at a respiratory volume corresponding to the body weight and at a respiration frequency of 80/min. A Harvard pump type 681 is used as respirator.

Thereupon, the arteria carotis is dissected bare from the same skin incision, a catheter being bound in. The registration of the respiratory pressure is effected via a pressure transducer connected to the respiration tube by a T-piece.

After dissection it is waited for at least 10 min in order to gain stable initial values. Thereafter, the zero point is determined and after further two to three minutes 150 mg immunoglobulin/kg body weight of i.v. applicable immunoglobulin G are intraarterially injected within 90 s via the catheter.

After 20 min, 50 mg standard substance/kg body weight are intraarterially injected within 90 s.

The maximum increase in the respiratory pressure during the 20 min following upon the injection of the sample is determined and compared to the initial mean value.

The bronchospastic effect of i.v. applicable immunoglobulin G is determined by injecting 500 mg/kg body weight of guinea pig intraarterially and comparing the average respiratory pressure in percent of four guinea pigs with the respiratory pressure increasing effect of i.m. applicable immunoglobulin G, standard substance.

Immunoglobulin-G-containing fractions according to the invention, which are free of side effects in an optimum manner, may be produced in that a fraction obtained from human or animal blood is treated with pancreas enzymes bound to water insoluble carrier material, such as trypsin or chymotrypsin or pancreas protease, and the treated fraction, if desired, is subjected to further fractionation and concentration.

Advantageously, Sepharose 4 B-Gel ® used as water insoluble carrier material.

The purified immunoglobulin can be precipitated from the immunoglobulin-containing fraction treated with enzymes bound to water insoluble carrier material, if desired after removal of undesired accompanying substances, by protein precipitating agents and processed into a final product.

In particular, a combination of the following purification and concentration measures has proved successful:

precipitating an immunoglobulin-containing precipitate from human or animal plasma by treatment with ethanol at a temperature of below 0° C.;

extracting the precipitate by means of a buffer solution and recovering from the obtained solution a paste-like immunoglobulin concentrate by further treatment with ethanol;

purifying this concentrate by dialysis;

treating the thus purified immunoglobulin-containing fraction with an immobilized enzyme from the group of trypsin, chymotrypsin or pancreas protease at an elevated temperature of about 37° C.;

precipitating from the thus treated fraction purified immunoglobulin substantially comprised of IgG by means of a protein precipitating agent, preferably polyethylene-glycol, and dissolving the precipitate, sterile filtering the solution and finally lyophilizing.

The production of the fractions according to the invention will be explained in more detail by the following working instructions and examples.

Working instructions for the preparation of an immobilized enzyme.

WORKING INSTRUCTION 1

1 l Sepharose 4 B-Gel ® (Pharmacia), after washing in 4 l of distilled water, is admixed with 200 g bromocyan dissolved in 100 ml acetonitrile at a pH of 11.0. The reaction mixture is cooled by an icebath. After removal of the liquid phase, the gel is mixed with 800 mg trypsin (Sigma) dissolved in 1 l 0.2 molar $NaHCO_3$. The trypsin that has not bound is separated by filtration from the trypsin that has bound to the gel.

After mixing the immobilized trypsin with 1 l of a 1 molar glycine solution, it is thoroughly washed free of proteins by a 0.2 molar $NaHCO_3$ solution. Finally, the immobilized trypsin is suspended in 1 l 0.9% NaCl solution—it is ready for use for incubation with an immunoglobulin fraction.

WORKING INSTRUCTION 2

The insoluble enzyme is prepared in the same manner as in Working Instruction 1, instead of trypsin, pancreas protease (Merck) is used.

WORKING INSTRUCTION 3

Working Instruction 1 is repeated, instead of trypsin, alpha-chymotrypsin (Sigma) is used.

Examples for the preparation of the immunoglobulin-G-containing fraction.

EXAMPLE 1

Human blood plasma is mixed with 8% ethanol at a pH of 7.2 and a temperature of $-2°$ C. After separation of the precipitate, the ethanol concentration is increased to 25% and the temperature is lowered to $-6°$ C. simultaneously. The precipitate, which contains immunoglobulin, is further purified by extraction with a phosphate acetate buffer and is mixed with 12% ethanol at a pH of 5.4 and a temperature of $-2°$ C.

The precipitate (containing alpha- and beta-globulin) is discarded. The ethanol concentration of the supernatant is increased to 25% at a pH of 7.2 and a temperature of $-10°$ C. The precipitated paste-like immunoglobulin is collected and the ethanol is removed by dialysis.

Thereafter, 170 g/l of ammonium sulfate are added to the dialysate at a pH of 6.25, the precipitate is separated and discarded. Further ammonium sulfate is added to the supernatant at a pH of 7.2 up to a concentration of 280 g/l. The precipitate is dissolved in water and dialyzed to remove the ammonium sulfate.

After dialysis the ionic strength of the immunoglobulin solution is adjusted to 0.15.

100 g immunoglobulin are prepared with 30 ml trypsin immobilized according to Working Instruction 1 and treated for 72 hours at 37° C. After removal of the immobilized trypsin, the treated immunoglobulin is precipitated by 135 g/l of polyethyleneglycol 4000. The precipitate is dissolved in 0.9% NaCl., sterile filtered, filled in containers and rendered storable by lyophilization.

EXAMPLE 2

The recovery of the immunoglobulin-containing fraction takes place in the same manner as in Example 1.

Incubation is effected by the immobilized pancreas protease prepared according to Working Instruction 2. 100 g immunoglobulin are treated with 70 ml gelatinous immobilized pancreas protease and maintained at 37° C. for 70 hours. After removal of the gel, the supernatant is admixed with 75 g/l polyethyleneglycol 4000 and the precipitate containing impurities is discarded.

Further polyethyleneglycol 4000 is added to the supernatant up to a final concentration of 85 g/l. The precipitate formed is discarded.

By increasing the polyethyleneglycol concentration to 135 g/l, the purified immunoglobulin is precipitated and rendered storable as in Example 1.

EXAMPLE 3

The recovery of the immunoglobulin-G-containing fraction is realized in the same manner as in Example 1, yet the treatment with immobilized alpha-chymotrypsin at 37° C. is carried out for 72 hours.

The data of the immunoglobulin-G-containing fractions of the invention prepared according to Examples 1 to 3, i.e. the contents of monomer IgG molecules, the contents of functionally intact IgG molecules, the anticomplementary activity as well as the content of gammaglobulin at the electrophoretic separation were determined as described below. These values are illustrated in the following Tables as well as in the annexed Diagram I.

Diagram I illustrates an elution curve under the indicated conditions between 150 and 400 ml as well as the relative elution volume $V_e/V_o$. The curve indicates the protein contents of the individual fractions, measured at an extinction of 280 nm.

In the following Table 1, the $V_e/V_o$ ratio according to the gel permeation chromatography carried out for the individual regions covered by the curve are indicated. As will be apparent, the $V_e/V_o$ ratio in the region of 1.30 to 2.20 is more than 90%.

TABLE 1

| | Gel permeation chromatography $V_e/V_o$ | | |
|---|---|---|---|
| | 1.0–1.29 | 1.30–2.20 | 2.21–2.70 |
| Example 1 | traces | 92.4% | 7.6% |
| Example 2 | — | 93.2% | 6.8% |
| Example 3 | — | 91.8% | 8.2% |

In Table 2 the ratio of the IgG molecules bound to protein A and the unbound IgG molecules is illustrated, the bound molecules corresponding to the functionally intact ones. As is apparent, the content of functionally intact IgG molecules in the total fraction is more than 90%.

TABLE 2

| | Affinity chromatography with protein A-Sepharose | | |
|---|---|---|---|
| | % of fraction $V_e/V_o$ 1.30–2.20 | | % of total immuno-globulin-G-contain- |
| | unbound | bound | ing fraction |
| Example 1 | 1.5 | 98.5 | 91.0 |
| Example 2 | 0.9 | 99.1 | 92.3 |
| Example 3 | 1.2 | 98.8 | 90.7 |

In Table 3 the values for the anticomplementary activity—obtained with the above modified determination method—and electrophoresis are indicated, from which it can be seen that, with the preparations of all the above Examples, values for the anticomplementary activity or more than 50 mg immunoglobulin-G-containing fraction were required to neutralize a C'H-50-unit and electrophoretically determined values of pure gammaglobulin of more than 97% were obtained.

TABLE 3

| | Anticomplementary activity | Electrophoresis |
|---|---|---|
| Example 1 | >50 mg/C'H-50 | >97.0% pure gamma-globulin |
| Example 2 | >50 mg/C'H-50 | >97.0% pure gamma-globulin |
| Example 3 | >50 mg/C'H-50 | >97.0% pure gamma-globulin |

The pharmacological characteristics and data values of the immunoglobulin-G-containing fractions of the invention prepared according to Examples 1 to 3, i.e. the vasoactive and the leucopenic effects in dog test and the bronchospastic effect in guinea pig tests, were determined as described above; these values are obvious from the following Tables.

TABLE 4

Average blood pressure of four dogs in % of initial value after injection of 500 mg of the preparation according to invention per kg body weight.

|  | Systolic blood pressure | Diastolic blood pressure |
| --- | --- | --- |
| Preparation according to Example 1 | 91% | 86% |
| Preparation according to Example 2 | 93% | 89% |
| Preparation according to Example 3 | 81% | 79% |

TABLE 5

Average leucocyte number of four dogs in % of initial value after injection of 500 mg of the preparation according to invention per kg body weight.

| Example 1 | 73% |
| --- | --- |
| Example 2 | 62% |
| Example 3 | 52% |

TABLE 6

Average respiratory pressure increase of four guinea pigs in % of initial value after injection of 500 mg of the preparation according to invention per kg body weight

| Example 1 | 102% |
| --- | --- |
| Example 2 | 110% |
| Example 3 | 125% |

The superiority of the intravenously applicable immunoglobulin-G-containing fractions to the known intramuscularly applicable ones will become clearly apparent from the annexed Diagrams II to IV.

In Diagram II the blood pressure curves with systolic and diastolic measurements in four dogs each are entered, the administered amounts in mg/kg body weight of the animals each being plotted on the abscissa. The full line in the region from A to B corresponds to the course of the blood pressure upon administration of the intravenously applicable immunoglobulin-G-containing preparations according to the invention; the course of the curve from A to C (full line and broken line) corresponds to the course of the blood pressure curve upon application of the i.m. standard substance. It is evident that upon application of the i.m. applicable standard substance at 5 mg/kg body weight the blood pressure has decreased by 30%, while upon application of the preparation according to the invention this decrease has occurred only at a dosage of 500 mg/kg body weight, i.e. the intravenously applicable immunoglobulin of the invention has a vasoactive effect that is at least 100 times less than that of known i.m. applicable preparations, under otherwise equal conditions.

From Diagram III the leucopenic effect in the dog test as an average of four animals is apparent as a comparison between the i.v. applicable preparation of the invention and the standardized i.m. applicable standard preparation. The full line in the region from A to B reflects the intravenously applicable immunoglobulin-G-containing preparation and the line from A to C (full line and broken line) indicates the course of the leucocyte number curve upon application of the i.m. applicable standard substance. It is apparent that upon application of the i.m. applicable standard substance the leucocytes have decreased by 50%, while upon application of the preparation according to the invention this decrease has occurred only at a dosage of 500 mg/kg body weight, i.e. the intravenously applicable immunoglobulin-G-containing preparation has a leucopenic effect that is at least 1,000 times less than that of known i.m. applicable preparations, under otherwise equal conditions.

A comparison of the bronchospastic effects in the guinea pig test according to Diagram IV looks similar, the course of the curve from A to B (full line) corresponding to the i.v. applicable preparation of the invention and the course of the curve from A to C (full line and broken line) corresponding to the standardized i.m. applicable preparation. The 30% increase in the respiratory pressure, with the known i.m. applicable preparation, occurs already at a dosage of 2 mg/kg body weight, while the same increase is observed with the i.v. applicable preparation only at a dosage of 500 mg/kg body weight, i.e. the bronchospastic side effect of the preparation according to the invention is 250 times less.

It has most surprisingly been found that immunoglobulin-G-containing fractions containing less than 90% IgG molecules capable of binding to protein A of staphylococcus aureus also exhibit the same valuable properties as the immunoglobulin-G-containing fractions described hereinbefore, which is illustrated on the basis of the following Examples:

EXAMPLE 4

Human blood plasma is mixed with 8% ethanol at a pH of 7.2 and a temperature of $-2°$ C. The precipitate obtained is separated and the ethanol concentration of the supernatant is increased to 25% at $-6°$ C. The precipitate obtained is separated and the immunoglobulin contained therein is further purified by extraction with a sodium acetate acetic acid buffer at a pH of 4.6. After addition of 12% ethanol at $-2°$ C., the alpha and beta globulins are removed by centrifugation and discarded. In the supernatant immunoglobulins are present in a purity of about 70%; they are concentrated by precipitation with 25% ethanol at a pH of 7 at $-6°$ C., centrifuged off and freeze dried for the removal of ethanol.

The powder is dissolved in an 0.9% NaCl solution and treated with immobilized trypsin (produced in accordance with working instruction 1) at 37° C. Upon removal of the immobilized trypsin, the supernatant is admixed with 65 g/l polyethyleneglycol 4000 and the precipitate, which contains impurities, is discarded. Further polyethyleneglycol is added to the supernatant to obtain a final concentration of 125 g/l.

The precipitate contains the immunoglobulins, it is dissolved in a NaCl-glucose buffer, sterile filtered, filled in containers and freeze dried.

EXAMPLE 5

Human blood plasma is mixed with 8% ethanol at a pH of 7.2 and a temperature of $-2°$ C. Upon separation of the precipitate formed, the ethanol concentration of the supernatant is increased to 25% at $-6°$ C. The precipitate forming, which contains immunoglobulin, is separated and further purified by extraction with a sodium acetate acetic acid buffer at a pH of 5.1. After addition of 9% ethanol at $-2°$ C., the alpha and beta globulins are removed by centrifugation and discarded. The supernatant contains the immunoglobulins in a purity of about 70%, it is diafiltered against distilled water for removal of the ethanol and ultrafiltered by means of an ultrafiltering membrane PM 10 from Amicon, in order to concentrate the immunoglobulin.

The 5% immunoglobulin solution is treated with immobilized trypsin at a pH of 7.0 and a temperature of 37° C.

Upon removal of the immobilized trypsin, the supernatant is admixed with 65 g/l polyethyleneglycol 4000 and the precipitate, which contains impurities, is separated and discarded. Further polyethyleneglycol is added to the supernatant to obtain a final concentration of 130 g/l. The precipitate contains the immunoglobulins, it is dissolved in an NaCl-glucose buffer, sterile filtered, filled in containers and freeze dried.

In the following Table 7, the $V_e/V_o$ ratio according to the gel permeation chromatography carried out for the individual regions of the curve are indicated. As will be apparent, the $V_e/V_o$ ratio in the region of 1.30 to 2.20 is in the order of 70%, i.e. 71.3 and 73.5, respectively.

TABLE 7

| | Gel permeation chromatography $V_e/V_o$ | | |
|---|---|---|---|
| | 1.0–1.29 | 1.30–2.20 | 2.21–2.70 |
| Example 4 | 20.7% | 71.3% | 8.0% |
| Example 5 | 19.3% | 73.5% | 7.2% |

In Table 8 the ratio of the IgG molecules bound to protein A and the unbound IgG molecules is illustrated, the bound molecules corresponding to the functionally intact ones. As is apparent, the content of the functionally intact IgG molecules in the total fraction is only in the range of 70%.

TABLE 8

| | Affinity chromatography with protein A-Sepharose | | |
|---|---|---|---|
| | % of fraction $V_e/V_o$ 1.30–2.20 | | % of total immunoglobulin-G-containing fraction |
| | unbound | bound | |
| Example 4 | 0.9 | 99.1 | 70.6 |
| Example 5 | 2.7 | 97.3 | 71.5 |

For determining the anticomplementary activity of the fractions obtained in Examples 4 and 5 a somewhat modified procedure was employed, which will be explained in more detail hereinafter.

It should first of all be noted that the determination of anticomplementary activity serves the purpose of safeguarding that only such products are used for intravenous injection that do not significantly activate the patient's complement system.

Complement is usually measured in 50 percent hemolytic units (C'H-50), because the curve of complement-mediated lyses approaches the 100% lyses value asymptotically and slight changes of complement concentration are best recognized in the vicinity of the 50% lyses point. The determination is carried out with the help of a standardized suspension of antibody-sensitized ovine erythrocytes, which is incubated with different dilutions of guinea pig serum serving as the source of complement. The degree of hemolysis is measured spectrophotometrically.

Aggregations of immunoglobulin can activate complement via Cl, i.e. upon incubation of the product to be tested with guinea pig serum, a consumption of complement is observed, which is called "anticomplementary activity". To determine the anticomplementary activity of the immunoglobulin product, test solutions are prepared which contain various amounts of the immunoglobulin product and 2 C'H-50-units of guinea pig serum per ml. These test solutions are first incubated for 18 hours at 4° C. After addition of the standardized antibody-sensitized erythrocyte suspension, the mixture is incubated for one hour at 37° C. After centrifugation, the absorbance (extinction) of the supernatant is measured at 541 nm. The absorbance values are plotted against the corresponding sample quantities in mg protein, and one determines the quantity of the product to be tested—in mg protein—which is required to reduce 2 C'H-50-units per ml by one unit (50% lysis of the erythrocytes).

The samples were prepared by reconstituting the lyophilized preparation with the necessary amount of a gelatin solution to obtain a 6% (w/v) solution, which was incubated for 1 hour at 37° C.

The ovine erythrocytes were prepared by mixing 1 part of ovine blood with an equal volume of a glucose-containing NaCl-Na citrate buffer solution and by storing the mixture under sterile conditions in 50 ml portions at 4° C. After one week of incubation the erythrocyte sediment was used for the preparation of the erythrocyte suspension.

For the erythrocyte suspension ovine erythrocytes were washed with a NaCl barbital buffer solution until the supernatant was clear (3–4 times). After centrifuging for 5 min at 1000 rpm packed erythrocytes were obtained. An approximately 2% erythrocyte suspension was prepared by adding 14 ml of an NaCl barbital buffer solution to 0.5 ml of packed erythrocytes. For determining the exact erythrocyte concentration, 2.5 ml distilled water were added to 0.5 ml of the erythrocyte suspension and the absorbance of the sample was read at 541 nm and 1 cm light path against distilled water. The reading should be between 0.98 and 1.01. If this is not the case, the previously prepared approximately 2% erythrocyte suspension must be corrected according to the following formula:

$$y = a \cdot A - a$$

y—buffer concentration still required (+) or in excess (−)

a—volume of erythrocyte suspension

A—absorbance of erythrocyte suspension

After correction of the erythrocyte concentration of the erythrocyte suspension by addition of packed erythrocytes or buffer solution, the measurement was repeated and the erythrocyte suspension stored in the refrigerator for later use.

A 1% antibody-sensitized erythrocyte suspension was prepared by mixing equal volumes of erythrocyte suspension and Amboceptor solution and by incubating the same for 30 min at room temperature.

For the preparation of a guinea pig serum pool with high complement activity the following procedure was followed:

Blood from 30–60 guinea pigs was collected by cardiac puncture and separately put into coned tubes. These tubes had been flushed before 10 times with distilled water and dried at 80° C. overnight to remove traces of detergent. The blood was incubated for 30 min at room temperature. After this, the erythrocytes sticking on the glass were carefully removed with a disposable stirring rod, and the tubes were then incubated for 1 hour at +4° C. Thereupon the erythrocytes were centrifuged for 5 min at 1000 g. Then the complement activity of the supernatant of each tube was determined. For this purpose a 1:201 dilution of the serum with a gelatin-containing NaCl barbital buffer solution was prepared. These serum dilutions were stored for later use at +4° C.

| Pipetting scheme in ml: | | | | | | | |
|---|---|---|---|---|---|---|---|
| buffer solution | 0.8 | 0.7 | 0.6 | 0.5 | 0.4 | — | 1.0 |
| diluted guinea pig serum | 0.2 | 0.3 | 0.4 | 0.5 | 0.6 | — | — |
| distilled water | — | — | — | — | — | 1.0 | — |

1 ml of the 1% antibody-sensitized erythrocyte suspension was added to each of the 7 test tubes, followed by an incubation for 1 hour at 37° C. with occasional shaking. Upon centrifuging for 5 min at 1000 g, the absorbance of the supernatant at 541 nm and 1 cm light path was immediately measured against distilled water. When the absorbance of the water control amounted to A=1, the C'H-50-units per ml were calculated by plotting ml of diluted guinea pig serum against the corresponding absorbance values as A/(1-A) on double logarithmic paper. A reading of the ml serum dilution corresponding to A/(1-A)=1 (corresponding to A=0.5) was made and used in the following formula: C'H-50-units per ml of guinea pig serum $$\frac{1}{x}.$$

dilution factor x - ml of serum dilution resulting from the graphs.

All the samples having more than 400 C'H-50 units/ml were pooled and stored in 1.1 ml aliquots at −20° C.

For the standadization of guinea pig serum to a new erythrocyte preparation, guinea pig serum was pre-diluted with buffer 1:4.5, 1:5 and 1:5.5, followed by a further 1:40 dilution of each. The samples were kept at +4° C. and propagated as described below:

| Pipetting scheme in ml: | | | | | | |
|---|---|---|---|---|---|---|
| buffer solution | 1.7 | 1.6 | 1.5 | 1.4 | — | 2.0 |
| diluted guinea pig serum | 0.3 | 0.4 | 0.5 | 0.6 | — | — |
| distilled water | — | — | — | — | 2.0 | — |

The samples were well mixed, admixed with 1 ml of the 1% antibody sensitized erythrocyte suspension and incubated for 1 hour at 37° C. Upon centrifuging for 5 min at 1000 g the absorbance of the supernatant at 541 nm and 1 cm light path was immediately measured against distilled water. The C'H-50-units per ml of guinea pig serum from each dilution series were calculated as described above and multiplied by the corresponding predilution factor. An average value for the predilution standing for 1/40 C'H-50-units/ml guinea pig serum was calculated. This value was divided by two to obtain the dilution factor by which the guinea pig serum had to be diluted to yield 80 C'H-50-units per ml with the erythrocyte suspension used in the test.

For determining the anticomplementary activity of the immunoglobulin samples, the sample was diluted with buffer according to the following pipetting scheme in ml.

| Sample | dilution | | | | |
|---|---|---|---|---|---|
| | 1:2 | 1:4 | 1:8 | 1:16 | 1:32 |
| Glucose-NaCl-solution | — | 0.5 | 0.75 | 0.875 | 0.935 | 0.9687 |
| Sample solution | 1 | 0.5 | 0.25 | 0.125 | 0.0625 | 0.0313 |

| -continued | | | | | | |
|---|---|---|---|---|---|---|
| Guinea pig serum (80 C'H-50/ml) | 0.025 | 0.025 | 0.025 | 0.025 | 0.025 | 0.025 |
| Buffer solution | 1 | 1 | 1 | 1 | 1 | 1 |
| Controls: | | Buffer control | | GP2 | | GP1 |
| Glucose-NaCl-solution | | 1 | | 1 | | 1 |
| Buffer-solution | | 1 | | 1 | | 1.0125 |
| Guinea pig serum (80 C'H-50/ml) | | — | | 0.025 | | 0.0125 |

One mixed well and incubated for 18 hours at +4° C. Then 1 ml of the 1% antibody-sensitized erythrocyte suspension was added to each sample, followed by incubation for 1 hour at 37° C. A lysis control was prepared by mixing 1 ml distilled water with 1 ml of the erythrocyte suspension. After centrifuging for 5 min at 1000 g, the absorbance of the supernatant at 541 nm and 1 cm light path was immediately measured against distilled water.

For the standard determination of guinea pig serum: The following test was used to confirm the guinea pig serum dilution obtained from the procedure described above in each individual anticomplementary activity determination. For this purpose, the serum was first pre-diluted by the average dilution factor and subsequently a 1:40 dilution was prepared therefrom. The C'H50 units were calculated as described above.

The absorbances were plotted against the corresponding amount of the reconstituted product in mg (60 mg/30 mg/15 mg/7.5 mg/3.75 mg) and the mg amount of product necessary to reduce the absorbance of the supernatant to 0.5 was determined. The result indicates the quantity of the product tested (in mg protein) that is required to reduce 2 C'H-50-units per ml by one unit.

The test is only valid, if lysis control yields an absorbance value between 0.98—1.02 and if, in addition, the complement controls yield absorbance values between 0.9 and 1 (GP2) and 0.4—0.6 (GP1). The buffer control may not exceed 0.01 absorbance units, and the C'H-50-units obtained with the standard determination of guinea pig serum should be within the range of 1.9–2.1 units per ml.

The following Table 9 gives the values for the anticomplementary activity of the fractions obtained in Examples 4 and 5 and calculated in accordance with the procedure explained in greater detail hereinbefore, as well the electrophoresis values, which latter show that the purity of the gammaglobulin was in the range of 70% only.

TABLE 9

| | Anticomplementary activity | Electrophoresis (% pure gammaglobulin) |
|---|---|---|
| Example 4 | 1.9 mg/C'H-50 | 70.1 |
| Example 5 | 2.5 mg/C'H-50 | 71.3 |

The pharmacological characteristics and data of the immunoglobulin-G-containing fractions of the invention prepared according to Examples 4 and 5, i.e. the vasoactive and leucopenic effects in dog test and the bronchospastic effect in guinea pig test, determined as hereinbefore described, can be seen from the following Tables.

TABLE 10

Average blood pressure of four dogs in % of initial value after injection of 500 mg of the preparation according to invention per kg body weight.

|  | Systolic blood pressure | Diastolic blood pressure |
|---|---|---|
| Preparation according to Example 4 | 84% | 79% |
| Preparation according to Example 5 | 74% | 71% |

TABLE 11

Average leucocyte number of four dogs in % of initial value after injection of 500 mg of the preparation according to invention per kg body weight.

| Example 4 | 55% |
|---|---|
| Example 5 | 51% |

TABLE 12

Average respiratory pressure increase of four guinea pigs in % of initial value after injection of 500 mg of the preparation according to invention per kg body weight

| Example 4 | 125% |
|---|---|
| Example 5 | 117% |

On account of the chemical composition and the pharmacological properties, the immunoglobulin-G-containing fractions according to the invention are excellently suited for use in the treatment of primary and secondary immune defects, A-gammaglobulinemia or hypogammaglobulinemia, antibody deficiency syndrome, virus infections or bacterial infections as well as autoimmune or immune complex diseases.

What we claim is:

1. An immunoglobulin-G-containing fraction from human or animal plasma, comprising monomeric IgG molecules and suited for intravenous application, wherein at least 90% IgG molecules capable of binding to protein A of staphylococcus aureus are contained, which fraction has an anticomplementary activity of $>50$ mg/C'H-50 and is substantially free of vasoactive and leucopenically active as well as bronchospastic substances, expressed by the following characteristic features:

(a) the vasoactive effect in dog test as an average of four animals comprising a blood pressure decrease of less than 30%, is detectable only at a dose of more than 500 mg/kg body weight,
    (b) the leucopenic effect in dog test as an average of four animals comprising a decrease in the number of leucocytes of 50% at the most, is detectable only at a dose of more than 500 mg/kg body weight, and
    (c) the bronchospastic effect in guinea pig test as an average of four animals comprising an increase in the respiratory pressure of less than 30%, is detectable only at a dose of more than 500 mg/kg body weight.

2. A method for the treatment of primary and secondary immune defects, A-gammaglobulinemia or hypogammaglobulinemia, antibody deficiency syndrome, virus infections, bacterial infections, autoimmune or immune complex diseases, said method comprising administering an immunoglobulin-G-containing fraction as set forth in claim 1.

3. A pharmaceutical composition of matter for use in the treatment of primary and secondary immune defects, A-gammaglobulinemia or hypogammaglobulinemia, antibody deficiency syndrome, virus infections, bacterial infections, autoimmune or immune complex diseases, said composition comprising an immunoglobulin-G-containing fraction as set forth in claim 1.

4. An immunoglobulin-G-containing fraction from human or animal plasma, comprising monomeric IgG molecules and suited for intravenous application, wherein at least 70% IgG molecules capable of binding to protein A of staphylococcus aureus are contained, which fraction has an anticomplementary activity of $>1.9$ mg/C'H-50 and is substantially free of vasoactive and leucopenically active as well as bronchospastic substances, expressed by the following characteristic features:

(a) the vasoactive effect in dog test as an average of four animals comprising a blood pressure decrease of less than 30%, is detectable only at a dose of more than 500 mg/kg body weight,
    (b) the leucopenic effect in dog test as an average of four animals comprising a decrease in the number of leucocytes of 50% at the most, is detectable only at a dose of more than 500 mg/kg body weight, and
    (c) the bronchospastic effect in guinea pig test as an average of four animals comprising an increase in the respiratory pressure of less than 30%, is detectable only at a dose of more than 500 mg/kg body weight.

5. A method for the treatment of primary and secondary immune defects, A-gammaglobulinemia or hypogammaglobulinemia, antibody deficiency syndrome, virus infections, bacterial infections, autoimmune or immune complex diseases, said method comprising administering an immunoglobulin-G-containing fraction as set forth in claim 4.

6. A pharmaceutical composition of matter for use in the treatment of primary and secondary immune defects, A-gammaglobulinemia or hypogammaglobulinemia, antibody deficiency syndrome, virus infections, bacterial infections, autoimmune or immune complex diseases, said composition comprising an immunoglobulin-G-containing fraction as set forth in claim 4.

* * * * *